(12) United States Patent
Melamed (10) Patent No.: US 10,912,511 B2
(45) Date of Patent: Feb. 9, 2021

(54) MEASURMENT OF NURSED BREAST MILK (71) Applicant: Ofer Melamed, Rehovot (IL)

(72) Inventor: Ofer Melamed, Rehovot (IL)

(73) Assignee: Ofer Melamed, Rehovot (IL)

( * ) Notice: Subject to any disclaimer, the term of this patent is extended or adjusted under 35 U.S.C. 154(b) by 619 days.

(21) Appl. No.: 14/786,229

(22) PCT Filed: Apr. 9, 2014

(86) PCT No.: PCT/IL2014/050344
§ 371 (c)(1),
(2) Date: Oct. 22, 2015

(87) PCT Pub. No.: WO2014/174508
PCT Pub. Date: Oct. 30, 2014

(65) Prior Publication Data
US 2016/0058361 A1    Mar. 3, 2016

Related U.S. Application Data (60) Provisional application No. 61/814,831, filed on Apr. 23, 2013.

(51) Int. Cl.
*A61B 5/00* (2006.01)
*A61B 5/145* (2006.01)
(Continued)

(52) U.S. Cl.
CPC .......... *A61B 5/4288* (2013.01); *A61B 5/0075* (2013.01); *A61B 5/14507* (2013.01);
(Continued)

(58) Field of Classification Search
None
See application file for complete search history.

(56) References Cited

U.S. PATENT DOCUMENTS

| 196,594 A | * | 10/1877 | Patch | .................... A61F 13/141 |
| | | | | 128/890 |
| 3,790,016 A | | 2/1974 | Kron | |

(Continued)

FOREIGN PATENT DOCUMENTS

| EP | 0077413 | 4/1983 |
| EP | 2273920 | 1/2011 |

(Continued)

OTHER PUBLICATIONS

Arora et al., (2000) Major factors influencing breastfeeding rates: Mother's perception of father's attitude and milk supply. Pediatrics 106(5): E67; 7 pages.

(Continued)

*Primary Examiner* — Matthew Kremer
(74) *Attorney, Agent, or Firm* — Allan A. Fanucci (57) ABSTRACT

A nursing monitoring device includes an inlet conduit with an inlet opening to enable milk that is released from a nipple to enter the inlet conduit. An outlet conduit with an outlet opening enables milk from the outlet conduit to enter a mouth of a nursing child. A measurement unit connected to the inlet conduit and to the outlet conduit enables measurement of a property of the milk that flows from the inlet conduit to the outlet conduit via the measurement unit. The outlet conduit is sufficiently long to enable placement of the measurement unit laterally to the mouth.

19 Claims, 5 Drawing Sheets

(51) Int. Cl.
- *G01N 33/04* (2006.01)
- *G01N 33/487* (2006.01)
- *A61B 10/00* (2006.01)
- *A61B 5/103* (2006.01)
- *A61B 5/1455* (2006.01)

(52) U.S. Cl.
CPC .......... *A61B 5/4312* (2013.01); *A61B 5/7271* (2013.01); *A61B 5/742* (2013.01); *A61B 5/7405* (2013.01); *A61B 10/0045* (2013.01); *G01N 33/04* (2013.01); *G01N 33/487* (2013.01); *A61B 5/1032* (2013.01); *A61B 5/1455* (2013.01); *A61B 2562/0204* (2013.01); *A61B 2562/0271* (2013.01)

(56) References Cited

U.S. PATENT DOCUMENTS

| | | |
|---|---|---|
| 4,153,170 A | 5/1979 | Aquarian |
| 4,714,462 A | 12/1987 | DiDomenico |
| 5,151,082 A * | 9/1992 | Gorsuch ............ A61B 5/14528 210/645 |
| 5,259,068 A | 11/1993 | Carroll |
| 5,531,231 A | 7/1996 | Morrissey et al. |
| 5,664,828 A | 9/1997 | Simon |
| 5,827,179 A | 10/1998 | Lichter |
| 5,827,191 A | 10/1998 | Rosenfeld |
| 6,109,100 A * | 8/2000 | Buckley ............ A61J 9/00 604/76 |
| 6,264,529 B1 | 7/2001 | Logue |
| 7,621,797 B1 * | 11/2009 | Hershkovich ............ A41C 3/04 450/36 |
| 8,511,180 B2 | 8/2013 | Melamed |
| 2002/0169391 A1 * | 11/2002 | Hung ............ A61B 10/0041 600/562 |
| 2003/0046983 A1 * | 3/2003 | Sato ............ G01N 7/00 73/53.01 |
| 2005/0177099 A1 * | 8/2005 | Dahan ............ A61B 5/4288 604/76 |
| 2005/0283327 A1 | 12/2005 | Bowman et al. |
| 2006/0179542 A1 | 8/2006 | Pierce et al. |
| 2007/0119810 A1 | 5/2007 | Boles |
| 2008/0022765 A1 * | 1/2008 | Witt ............ G01F 3/16 73/199 |
| 2008/0039741 A1 | 2/2008 | Shemesh et al. |
| 2008/0077040 A1 | 3/2008 | Ales et al. |
| 2008/0077042 A1 | 3/2008 | Feldkamp et al. |
| 2008/0097169 A1 | 4/2008 | Long et al. |
| 2008/0108882 A1 | 5/2008 | Garbin |
| 2008/0167579 A1 | 7/2008 | Ezra et al. |
| 2009/0054771 A1 | 2/2009 | Kolberg et al. |
| 2009/0145851 A1 * | 6/2009 | Witt ............ G01N 30/32 210/741 |
| 2010/0074058 A1 | 3/2010 | Campbell |
| 2010/0217148 A1 | 8/2010 | Binder |
| 2010/0292604 A1 | 11/2010 | Kapon et al. |
| 2011/0111513 A1 * | 5/2011 | Baumann ............ G01N 33/6848 436/89 |
| 2012/0165730 A1 | 6/2012 | McCoy |
| 2014/0276198 A1 * | 9/2014 | Dunung ............ A61B 5/036 600/561 |
| 2014/0364758 A1 * | 12/2014 | Schindhelm ............ A61B 10/0051 600/531 |

FOREIGN PATENT DOCUMENTS

| | | | |
|---|---|---|---|
| GB | 2460846 | 12/2009 | |
| WO | WO 9215196 A1 * | 9/1992 | ............ A01J 5/045 |
| WO | 0009006 | 2/2000 | |
| WO | 0154488 | 8/2001 | |
| WO | 2005/077264 | 8/2005 | |
| WO | 2007/078810 | 7/2007 | |
| WO | 2009132334 | 10/2009 | |

OTHER PUBLICATIONS

Casoli et al., (2008) Optimization of relevant design parameters of external gear pumps. Proceedings of the 7th JFPS International Symposium on Fluid Power, Toyama, Japan; Sep. 15-18, 2008. P1-05; 6 pages.

Cox et al., (1996) Blood and milk prolactin and the rate of milk synthesis in women. Exp Physiol 81(6): 1007-1020.

Geddes et al., (2008) Tongue movement and intra-oral vacuum in breastfeeding infants. Early Hum Dev 84(7):471-477.

Laogun (1986) Dielectric properties of mammalian breast milk at radiofrequencies. Phys Med Biol 31(5): 555-561.

Noolridge (1986) the 'anatomy' of infant sucking. Midwifery 2(4): 164-171.

* cited by examiner

# MEASURMENT OF NURSED BREAST MILK

CROSS REFERENCE TO RELATED APPLICATIONS

This patent application is a U.S. National Phase filing of commonly owned PCT Application No. PCT/IL2014/050344, filed Apr. 9, 2014, which is based on and claims the benefit of the filing date of U.S. Provisional Patent Application Ser. No. 61/814,831, filed Apr. 23, 2013, both which are incorporated herein by reference in their entirety.

FIELD OF THE INVENTION

The present invention relates to measurement of liquid flow. More particularly, the present invention relates to measurement of breast-milk while a baby is nursing.

BACKGROUND OF THE INVENTION

The experience of breastfeeding is valued by mothers for many reasons. The reasons include bonding with the nursing child and the health benefits for both mother and child. Breastfeeding protects young children babies from the risks of a contaminated water supply. Studies have indicated that breastfeeding can help protect against respiratory illnesses and diarrhea, diseases that can be fatal in some populations, e.g., those displaced by natural or manmade disasters. Breast milk is at a temperature that helps to prevent hypothermia in the nursing child. Breast milk is readily available without incurring additional expense.

However, nursing mothers often are concerned about how often to breastfeed their child and whether the child is receiving sufficient nourishment from nursing.

Scales are often used to measure breastfeeding success. Health care providers may weigh babies before and after feedings may advise mothers that they do not produce enough milk if the result is not deemed. Sometimes, a mother may wean her baby unnecessarily, when the actual problem is faulty interpretation of the weight data. Counting wet and soiled diapers may provide reassurance that a baby is getting enough milk for hydration and growth. Such methods may be misleading.

Pumping breast milk may enable measurement of intake, but in some cases may be excessively tedious or difficult.

SUMMARY OF THE INVENTION

There is thus provided, in accordance with an embodiment of the present invention, a nursing monitoring device including: an inlet conduit with an inlet opening to enable milk that is released from a nipple to enter the inlet conduit; an outlet conduit with an outlet opening to enable milk from the outlet conduit to enter a mouth of a nursing child; and a measurement unit connected to the inlet conduit and to the outlet conduit to enable measurement of a property of the milk that flows from the inlet conduit to the outlet conduit via the measurement unit, the outlet conduit being sufficiently long to enable placement of the measurement unit laterally to the mouth.

Furthermore, in accordance with some embodiments of the present invention, the measurement unit includes a flowmeter.

Furthermore, in accordance with some embodiments of the present invention, the flowmeter includes a positive displacement meter.

Furthermore, in accordance with some embodiments of the present invention, the positive displacement meter includes a gear.

Furthermore, in accordance with some embodiments of the present invention, the flowmeter is selected from a group of flowmeter types consisting of a membrane movement meter, an inflatable balloon meter, a piston meter, a nutating disk displacement meter, an oval gear meter, and a helical gear meter.

Furthermore, in accordance with some embodiments of the present invention, the flowmeter is configured to produce an electronic signal that is indicative or a volume or flow rate of milk that flows through the flowmeter.

Furthermore, in accordance with some embodiments of the present invention, the flowmeter includes a rotation counter.

Furthermore, in accordance with some embodiments of the present invention, the measurement unit includes a window to enable visual examination of flowing milk.

Furthermore, in accordance with some embodiments of the present invention, the measurement unit includes a valve to enable extraction of a sample of the flowing milk.

Furthermore, in accordance with some embodiments of the present invention, the device includes a processing unit for processing data that is measured by the measurement unit, the processing unit being connectible via a data cable or via a wireless connection to the measurement unit.

Furthermore, in accordance with some embodiments of the present invention, the processing unit includes a display screen or an audible output device.

Furthermore, in accordance with some embodiments of the present invention, the outlet opening is located on an artificial nipple.

Furthermore, in accordance with some embodiments of the present invention, the device includes a nursing cup, wherein the inlet opening is located on an inner side of the nursing cup.

Furthermore, in accordance with some embodiments of the present invention, the outlet opening is located on an outer side of the nursing cup.

Furthermore, in accordance with some embodiments of the present invention, the outlet opening is located substantially opposite the inlet opening.

Furthermore, in accordance with some embodiments of the present invention, the inlet conduit and the outlet conduit are enclosed in a single tube.

Furthermore, in accordance with some embodiments of the present invention, the measurement unit includes an interferometer, a spectrophotometer, an acoustic sensor, a timer, or a thermometer.

There is further provided, in accordance with some embodiments of the present invention, a method for monitoring breastfeeding, the method including: placing an inlet opening on a nipple to enable milk that is released from the nipple to enter an inlet conduit via the inlet opening and to flow via the inlet conduit into a measurement unit to an outlet conduit; placing an outlet opening of the outlet conduit at a position that is accessible to a mouth of a nursing child such that the measurement unit is located laterally to the mouth; and operating the measurement unit to measure a property of the milk that flows from the inlet conduit to the outlet conduit.

Furthermore, in accordance with some embodiments of the present invention, operating the measurement unit includes observing the flowing milk via a window, extracting a sample of the milk, or operating a measurement device selected from a group of measurement devices consisting of a flowmeter, an interferometer, a spectrophotometer, an acoustic sensor, a timer, and a thermometer.

Furthermore, in accordance with some embodiments of the present invention, placing the inlet opening and the outlet opening includes placing a nursing cup on the nipple.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

DETAILED DESCRIPTION OF THE INVENTION

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless explicitly stated otherwise, any use of the conjunction "or" should be understood as inclusive.

Embodiments of the invention may include an article such as a computer or processor readable medium, or a computer or processor non-transitory storage medium, such as for example a memory, a disk drive, or a USB flash memory, encoding, including or storing instructions, e.g., computer-executable instructions, which when executed by a processor or controller, carry out methods disclosed herein.

In accordance with an embodiment of the present invention, a nursing monitoring device enables measurement of breast milk that is provided to a child during nursing. The device includes a structure that is placed over the nipple of the breast from which the child is nursing. (For convenience, the person whose nipple is providing the milk may be referred to herein as a mother. Use of the term "mother" should not be understood as excluding a wet nurse or other person who is providing the milk. Similarly, although reference is made herein to a human nipple and child, devices and methods described herein may be applicable to teats and young of at least some other mammalian species.) The device includes an inlet opening through which milk from the nipple may enter a proximal end an inlet conduit to a measurement unit connected to a distal end of the inlet conduit. The milk passes through the inlet conduit and the measurement unit and into a distal end of an outlet conduit. The outlet conduit conducts the milk to an outlet opening at a proximal end of the outlet conduit. The output opening is configured to enable the milk to flow into the child's mouth. The measurement unit, when in use, is located laterally to the output opening such that when the child is nursing via the monitoring device, the measurement unit may be placed or located laterally to the child's mouth. For example, a length of the outlet conduit is sufficiently long to enable placement of the monitoring device laterally to the child's mouth. In some cases, the measurement unit is also located laterally to the nipple (e.g., to the areola). As used herein, a unit is considered to be located laterally to a mouth when the unit is located outside of the mouth (in any direction) such that no part of the unit is surrounded by or touches the lips or cheek of the child.

Such a monitoring device, where the measurement unit is not placed within a space between the nipple and the child's mouth may be advantageous. The size of the measurement unit is not constrained by any requirement to fit between the nipple and the child's mouth. Similarly, materials used in the conduits and measurement unit are not required to be flexible so as prevent discomfort during nursing as would be required if the measurement unit were to be placed between the nipple and child's mouth (e.g., in the form of an artificial nipple, brassiere, or similar device). The monitoring device may be closely adapted to the anatomy and physiology related to breastfeeding.

Reduction or elimination of size or flexibility requirements may allow for a lower cost measurement unit (e.g., not requiring specialized miniaturized components), or for increased accuracy measurement in measurement of the milk. Reduction or elimination of size or flexibility requirements may enable monitoring of the milk without interrupting or disturbing nursing by the child.

Reduction or elimination of size or flexibility requirements may enable incorporation of an increased variety of sensors into the measurement unit. Sensors need not be limited to those that are small enough to fit between the nipple and mouth. For example, a hemoglobin sensor for detection of traces of blood in the milk, an inflammation sensor to identify mastitis, or other sensors may be included. A manual or electric pump may be incorporated, e.g., to assist premature or weak babies by providing additional sucking force. An adjustable valve to control the rate of flow may be incorporated, e.g., to enable manipulation of the amount of milk produced by the breast, the rate of milk synthesis being influenced by evacuation of milk from the breast.

Placement of the measurement unit lateral to the child's mouth enables any electrical connectors or devices to be far removed from the child's mouth, face, or head. When the measurement unit is also place lateral to the nipple (e.g., lateral to the areola), irritation of the nipple area by the measurement unit (e.g., when the nipple area is cracked or sensitive) may be prevented, reduced, or eliminated. Lateral placement of the measurement unit may enable a structure (e.g., in the form of a cap) that includes the inlet and outlet openings to be made thin. The thin structure may be adapted so as not to interfere with the natural reflexes related to breastfeeding, such as the ejection reflex and the sucking reflex. Thus, a thin structure may enable mutual enjoyment of the nursing experience by both the mother and the child.

A nursing monitoring device, in accordance with embodiments of the present invention, may be adapted to natural nursing patterns in infants and older nursing children.

An infant is equipped with reflexes to initiate breastfeeding. Tactile stimulation triggers a rooting reflex in which the infant's head turns toward the nipple, and the child's mouth opens to accept the nipple. Since a newborn infant's mouth is open only briefly, reinforcement on the part of the mother is necessary. The sucking reflex is elicited by stimulating the palate by the nipple. The sucking reflex generates a fast burst (approximately 2 Hz) of sucking before the milk begins to flow, and a slower pace (approximately 1 Hz) after the milk has begun to flow. The presents of these two sucking patterns indicates that a delay in delivery of milk from the nipple to a child's mouth due to flow through conduits and a measurement unit may not interfere with natural patterns of nursing. The mean latency for release of milk after the start of suckling has been measured to be about 2.2 minutes. Intake during lactation sucking burst have been measured to average about 25 g to 35 g. At the start of feeding, each suck causes a volume of milk of 0.14 ml to be taken in, decreasing to about 0.10 ml.

Furthermore, the shape and characteristics of the nipple are well matched to the form and function of an infant's mouth. Thus, a monitoring device in which all rigid materials are positioned laterally to the infant's mouth may not interfere with this matching. The matching may be further preserved by making as thin as possible any sections that are designed to be positioned between the nipple and the mouth. Furthermore, the monitoring device may be designed to reduce, minimize, or eliminate movement of sections that are designed to be positioned between the nipple and the mouth (e.g., by using a fitted or adhesive nursing cap).

The measurement unit may include a flow indicator or measurement device. For example, a flow indicator may include a visible paddle wheel that rotates when milk flows through the device. The flow indicator may include a flowmeter that produces an electronic signal or other indication that is indicative of a rate of flow.

The measurement unit may enable evaluation of a quality of milk that flows through the measurement unit. For example, the measurement unit may include an optical or chemical sensor that produces an indication of a characteristic or property of the milk. The measurement unit may divert a fraction of the flowing milk to an external collection container (e.g., tube or bottle). A sample of the collected milk may then be evaluated using one or more physical, chemical, or biological evaluation techniques, Measurements made with a monitoring device in accordance with embodiments of the present invention may be utilized in surveys, experiments, and investigational studies, as well as assisting individual nursing mothers in evaluating the effectiveness of their breastfeeding. For example, ejection and the evacuation rates of breast milk may be conveniently measured.

Various possible problems and disorders related to nursing are known. Such problems include overproduction or underproduction of milk, sucking that is too weak (insufficient) or too strong (causing pain), unpleasant sensations, or other problems. Components of a nursing monitoring device in accordance with embodiments of the present invention may be adapted to alleviate or to not exacerbate a problem.

Modeling or simulation may enable design or optimization of a nursing monitoring device for a general or particular situation. Such a model may be based on mathematical or numerical modeling of nursing, or may be based on (actual or simulated) physical devices or components that mimic aspects of nursing.

During nursing, milk is released or ejected from lactiferous ducts in the central part of the nipple. Milk is propelled towards the back of the mouth by a posteriorly-directed, roller-like peristaltic wave along the surface of the tongue. This ejection process is driven by the squeeze of the tongue on the jaw. The process of milk ejection is repetitive is referred to as the suckling cycle. This expression reflex causes the active expulsion of milk into the infant mouth, with little or no involvement on the part of the infant. Milk is ejected from a breast in a positive-pressure pulsating patterns, analogously to, a positive-pressure pulsating and rhythmic pump. The rate of positive pressure mutually depends on the milk synthesis rates. The average short-term rate of milk synthesis has been calculated (e.g., from the increase in breast volume between breastfeeds) to be about 23 ml/h.

A child's mouth generates a negative pressure in order to cause the mouth to latch onto the breast and to remove milk from the nipple (thus stimulating the ducts in the nipple to refill). Peak vacuum (empirically measured at about $-145$ mm of mercury) occurs when the tongue is in its lowest position within the mouth. Milk flow from the nipple into the infant's mouth typically coincides with both the lowering of the tongue and peak vacuum.

The combination of positive pressure in the ducts and negative suction pressure at the nipple surface act to maintain a pressure gradient in the duct system. This pressure differential ensures transport of milk to the nipple.

Breast milk has been extensively characterized, both physically and chemically. For example, such properties as water content, density, and viscosity have been measured for various conditions such as temperature, mother's age, and other conditions.

For example, a nursing model may include positive and negative rhythmically pulsating pumps interconnected by a conduit. The transferred milk can be considered as a two-phase fluid or emulsion. The positive and negative pressures can be modeled by independent time-varying oscillating functions having representative amplitudes and frequencies. For example, a typical pressure function may have an (e.g., empirically derived) amplitude of about 0.2 atmospheres with a frequency of about 1-2 Hz. A milk synthesis rate may be on the order of 5 micro-liters per second.

A numerical simulation can evaluate the behavior of the milk flow as a function of the pressure sources, milk properties, and conduit specifications. Such a numerical simulation may use Navier-Stokes equations or other differential equations to model fluid dynamics. Simulations may assist in optimizing parameters of a nursing monitoring device. Parameters may be specific to, or may be optimized for, a particular child, nursing mother, or milk properties.

An analog setup may be utilized to simulate and analyze the behavior of the flowing milk. For example, such an analog setup may measure flow or transfer of liquid from a combination of a source container and peristaltic pump (simulating a breast) to a target container and vacuum pump (simulating a child's mouth) via a nursing monitoring device. The quantity of fluid (e.g., weight or volume) in each of the source and target containers may be monitored as a function of time. Digital outputs of the various measuring devices may be input to a processor or computer for analysis.

A nursing monitoring device in accordance with an embodiment of the present invention may include a component in the form of a thin cup or breast shield (e.g., about 70 mm in diameter) that fits over the nipple region of the breast. The cup may have a smaller diameter (e.g., diameter of about 30 mm) that covers, or partially covers, the nipple. The cup may be in the form of a thin flexible sheet and made of an elastic or resilient, thin, and flexible material. Other forms are possible and may be adapted to a particular breast.

The inlet and outlet conduits may be made of a rigid material to prevent a collapse that could block or interfere with passage of milk. In some cases, an outlet conduit to the child's mouth (e.g., which could be partially evacuated by sucking) may be sufficiently rigid to prevent or inhibit collapse. On the other hand, an outlet conduit from the nipple (e.g., to which positive pressure may be applied by the ejection reflex) may be more flexible than that outlet conduit.

A cup may be configured to form an inlet space between the nipple and an inward (toward the breast) facing surface of the cup. For example, the inward-facing surface may include an indentation. The inlet space may serve as a buffer for collection of milk when the sucking pressure or resistance in conduit results in evacuation of milk at a slower rate than milk secretion from the nipple. The inlet space may thus prevent a blockage of the nipple which could reduce a rate of milk production.

The inlet and outlet openings may include milk reservoirs, e.g., in the form of pockets for holding milk. Such milk reservoirs may prevent or inhibit blockage of the milk flow, for example, when the rate of milk production is high (overactive letdown) or when fast milk evacuation is recommended to increase total milk production. A milk reservoir may assist an infant with a poor latch-on reflex.

The inward facing side of the cup, intended to face the breast surface, may be shaped to match the shape of the breast. An adhesive, sticky, or tacky material can be added to support the cup on the breast. The material may be select to minimize irritation of the breast. The cup may be shaped such that the adhesives do not touch the areola or other sensitive areas of the breast. The cup may function when a soft pad such as medical gauze, or when an anti-bacterial or anti-inflammatory paste, is placed on the breast.

An outward facing side of the cup, intended to face the child's mouth, may be configured to mimic the feel of the mother's breast. The outward facing surface may include a skin-texture material or skin-like gel which may be stretchable and may feel like a breast surface. Examples of such materials include bio-compatible tapes, carbon nano-tubes and silicon, flesh-like rubber, prosthetic polymers, or other materials. In general, any food grade and medical-grade material known in the art may be used. The outward facing side may be textured with slits, grooves, foam, or sponge-like texture to assist in laterally distributing the milk to the child's tongue.

The thickness of the nursing cup may be sufficiently thin, e.g., to preserve the intimate bonding between a nursing mother and her child. Thermoplastic materials may be utilized to enable heat to flow between the nursing mother and the child.

The nursing cup may include one or more holes, openings, or bores to enable suction that is applied by the child's mouth to hold the cup to the breast. One or more of the holes may be provided with a non-return or check valve, such as a flexible rubber cap, plug, or flap. The check valve may maintain the vacuum to hold the cup to the breast after cessation of the suction.

The inlet and outlet conduits may have any shape (cross section), length, width or diameter, or other dimensions that enables a safe and free flow of milk. The conduits and other components that contact the milk may be constructed of inert materials. Such material may include, for example, silicone, polyethylene, polypropylene, polyolefin, nylon, thermoplastic elastomer, polytetrafluoroethylene (e.g., Teflon®), stainless steel, polycarbonate, or other materials. Components may be easily washable (e.g., dishwasher safe), microwaveable, and air dryable.

The conduits may be configured to facilitate milk flow by reducing fluid resistance. For example, cross sectional area may be made as large as practicable, walls may be smooth, and conduits may be as short and as straight as practicable. (A large conduit diameter may reduce pressure drops that could lead to cavitation.) Any included porous materials (e.g., at an outlet opening) may have pores that are as large as possible. (Flow resistance may increase with decreased pore size.) Suitable porous materials may include silicone, silicone compounds, nylon, or coated polymers. As another example, the nursing monitoring device may include a pump to overcome fluid resistance.

A wide, short conduit and smooth walls may also facilitate cleanliness and present bacterial or other contamination of the milk.

The inlet and outlet conduits may include multiple branches that converge into measurement unit. For example, multiple branches may reduce fluid resistance to the flow of the milk, or may reduce the possibility of blockage of the flow.

The inlet and outlet conduits may be configured for a particular child or type of child, such as for a child of a particular age. For example, the conduit diameter may be small when designed for a newborn infant, and larger for an older child. Different conduits may be configured for children of different size or weight, or for different breast and nipple shapes.

Walls of the inlet and outlet conduits may be sufficiently rigid (high Young modulus or large stiffness), sufficiently thick, to prevent collapse or bending during nursing.

The inlet and outlet conduits may be positioned next to each other (e.g., parallel, attached to one another, or enclosed in a single sleeve), or may extend in different directions.

The inlet and outlet conduits may have circular, elliptical, square, rectangular, polygonal, or otherwise shaped cross section. A circular cross section may provide the least resistance to flow. However, a flatter (e.g., ellipse with high eccentricity or rectangular) cross section may be more convenient in cases where a flat surface is desired.

The area of the cross section may be determined in consideration of fluid friction in the conduits and of their volume. The friction is inversely proportional with the cross section area. On the other hand, a large volume may delay the time required for the mild to reach the mouth (and risk spoilage of milk that remains in the conduit after nursing is finished.

For example, in some cases each conduit may have a cross sectional area of about 5 mm$^2$ and a length of about 20 mm. Such a conduit would, therefore, have a volume of about 100 mm$^3$.

The outlet opening may be nipple-shaped or may be located on an artificial nipple. The outlet opening may be located substantially opposite the inlet opening. In this manner, the outlet opening may be placed at the approximate location where the nursing child's mouth would be place in the absence of the nursing monitoring device. The outlet opening may be located at any point that is reachable by the mouth of the nursing child, and not necessarily opposite the nipple. The outlet opening may include more than one exit holes, slits, or openings. For example, an exit hole may be positioned near the base of the nipple shape may shorten the fluid path and reduce resistance to the flow. Multiple exit holes may prevent blockage (e.g., due to dirt or manufacturing flaws). Outflow through the outlet opening that is greater than flow through the inlet and outlet conduits may enable generation of a sucking pressure force sufficient to facilitate flow of the milk.

One or more valves may be provided to ensure a one-way flow of milk through the nursing monitoring device. A one-way valve may prevent milk or saliva from flowing backward through the measurement unit, possible leading to an erroneous measurement. A one-way valve may include, for example, a sealing disc that blocks an opening when a negative (wrong direction) pressure difference is applied. For example, the valve may include a silicone disc on top of the opening. The valve material may include a highly flexible material so as to minimize resistance to flow in the forward direction.

The measurement unit may include a transparent and rigid chamber that enables visual examination of the flowing milk. Visual examination may indicated whether milk is flowing, if there is blood mixed into the milk (e.g., when the milk has a reddish color), or if the color of the milk indicates a problem. For example, such a measurement unit may include a chamber made of transparent, rigid, and biocompatible nylon.

The measurement unit may include a walled chamber with flexible walls. Flow of milk through the flexibly walled chamber may case the chamber to swell in a manner that may be felt by the nursing mother or another person. A non-visual indication may be useful or convenient in the dark (e.g., at night).

The measurement unit may include a mechanical flowmeter. A mechanical flowmeter may include an arrangement of parts that are movable in response to the flow. For example, a moving part may include gears or paddles that divide the flowing fluid into metered volumes (positive displacement meter), or may include a turbine, rotor, or another moving part.

A positive displacement meter may provide high accuracy (e.g., ±0.1% of actual flow rate in some cases) and repeatability (e.g., as high as 0.05% of reading). Accuracy may not be affected by pulsating flow (unless air or gas is entrained in the flow). A positive displacement meter may not require a power supply for its operation and may not require a consistent upstream or downstream flow. Accuracy of a measurement using positive dependent flowmeter may be independent of conditions such as room temperature, body temperature, density or viscosity of the milk, and flow rate. (Inaccuracies may arise from trapped bubbles, from leakage, or from manufacturing defects.)

Performance of positive displacement meter with a gear may depend on the number and size of gear teeth, and on friction between the gear housing and the gear. The velocity of rotation depends on the milk flow rate and on the volume that is partitioned between the gear teeth. A torque that rotates the gear is proportional to the wheel diameter. A gear size may be selected to sufficiently small to be conveniently handled, while sufficiently large to reduce the required flow energy. The measurement resolution may depend on the partitioned volume. A counter may be configured to produce a signal each time a rotor tooth passes a sensor, the resolution of the device being half of the partitioned volume. A weight of the gear may be selected so as not to interfere with the nursing. For example, a heavy gear may require an extra effort to start the rotation, but once rotating it may be relatively in sensitive to bubbles in the milk and its inertia may maintain the rotation with less effort.

Use of a gear flowmeter may require application of a calibration technique known in the art so as to attain a required, desired, or optimal accuracy.

A positive displacement flowmeter may include a nutating disc meter. Milk flowing through the metering chamber causes a disc to nutate, turning a spindle which rotates a magnet. This magnet is coupled to a mechanical register or a pulse transmitter. Because the flowmeter entraps a fixed quantity of fluid each time the spindle is rotated, the rate of flow is proportional to the rotational velocity of the spindle.

Other types of mechanical flowmeters may include, for example, a rotating vane, turbine, piston, helix, or diaphragm flowmeter.

A measurement unit may include one or more components such as a sensor element, a voltmeter, a current meter, a temperature calibration component, a Wheatstone bridge, a memory device, or another suitable component.

Air bubbles in the milk may lead to a measurement error. To prevent air bubbles in the milk, a gas trap, as known in the art, may be incorporated into the flow line before the milk enters the measurement unit.

A nursing monitoring device in accordance with an embodiment of the present invention, in which the flow conduits are located laterally to the nursing child's mouth, may include a motorized pump, such a gear pump. For example, a pump may be operated when flow of the milk requires enhancement. Such situations may include, for example, when a newborn or premature infant is too weak to suck the milk, the breast has a blockage, when there time constraints, or in other situations.

Measurement or evaluation of milk quality may include determination of the aqueous or fatty composition of the milk, of oxygen saturation, or of $CO_2$ elimination. For example, a sample of the milk may be analyzed using an evaluation technique that may include application of a bio-sensors, testing paper, or spectral analysis of absorbed or transmitted light. Spectral analysis may indicate a composition of the aqueous solution, the fatty solution, oxygen binding to hemoglobin, or presence of traces of blood in the milk.

A nursing monitoring device in accordance with an embodiment of the present invention may be configured to regulate or control flow of the milk. For example, the device may include one or more valves, such as a check valve, a non-return valve, or a ratchet wheel. A valve may inhibit or prevent backflow which could lead to measurement error. An inlet or outlet opening may have an adjustable width or diameter to enable restriction of the flow of milk. For example, restriction of the flow may be applied during a weaning period or when the breast produces milk at an excessive rate.

Figure 1:
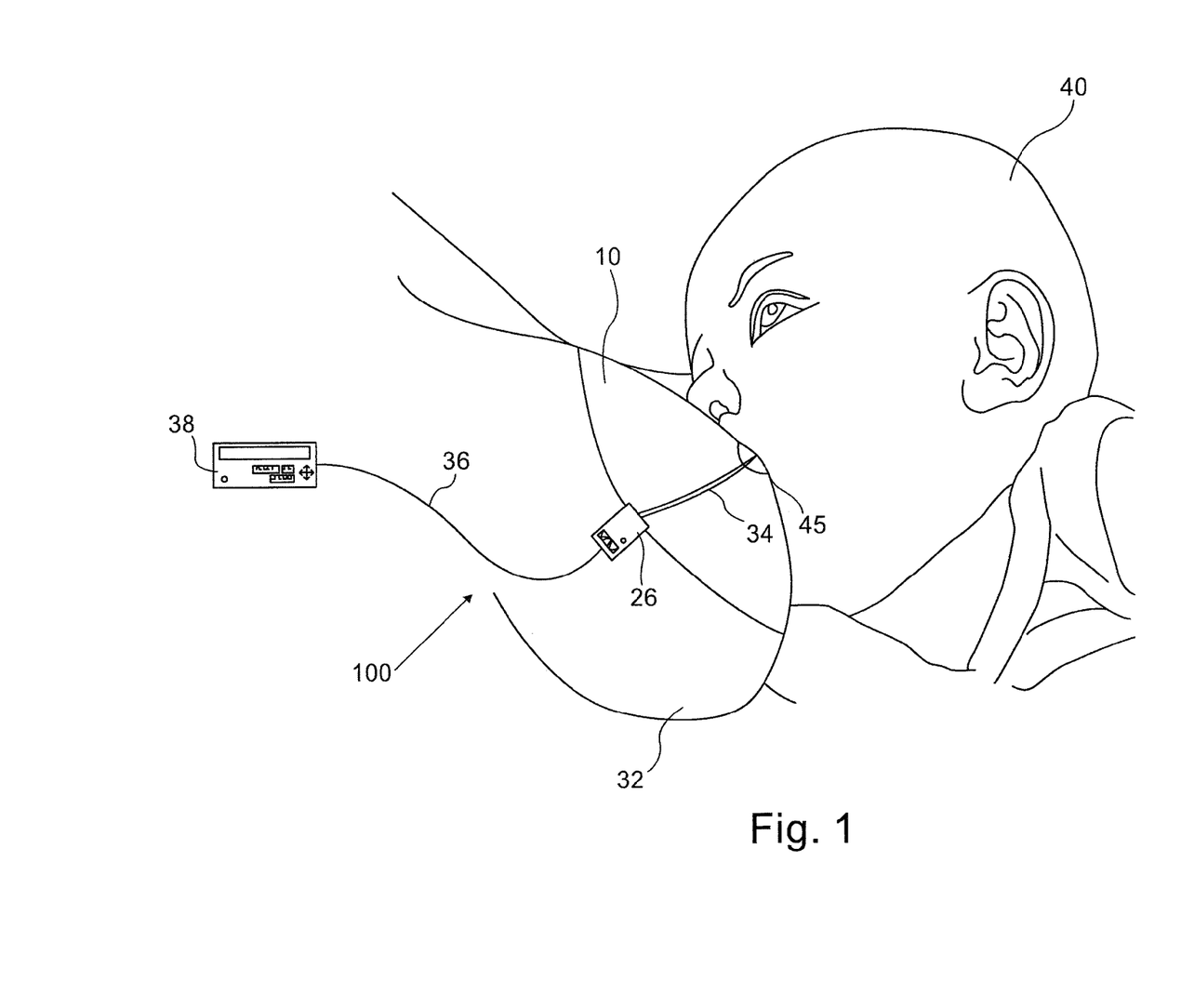
FIG. 1 is a schematic drawing of a nursing monitoring device in use, in accordance with an embodiment of the present invention.
Figure 2:
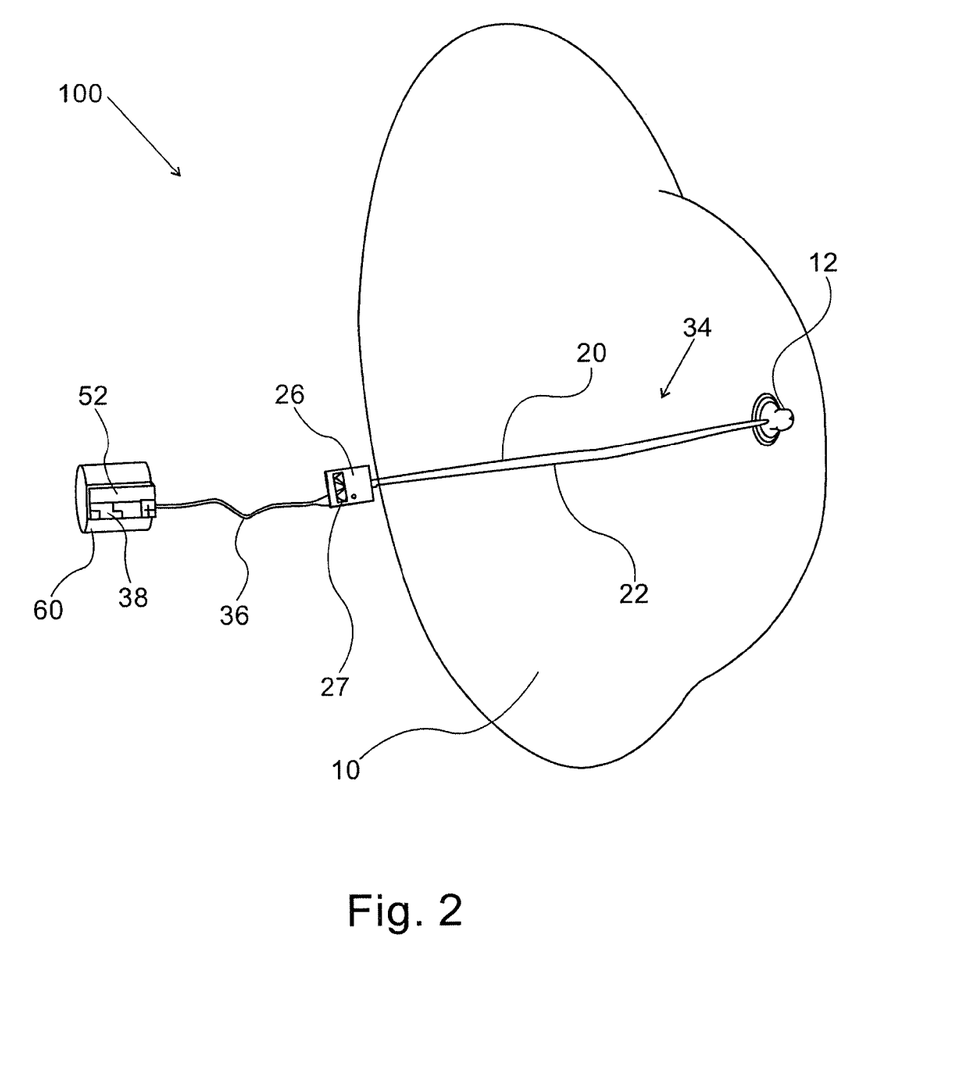
FIG. 2 is a schematic drawing of a nursing monitoring device, in accordance with an embodiment of the present invention.

FIG. 1 is a schematic drawing of a nursing monitoring device in use, in accordance with an embodiment of the present invention. FIG. 2 is a schematic drawing of a nursing monitoring device, in accordance with an embodiment of the present invention.

Nursing monitoring device 100 includes nursing cup 10 for placement on, reversible attachment to, and conformable to the shape of breast 32. Nursing cup 10 includes structure to enable milk to flow from breast 32 into conduit system 34. Conduit system 34 includes an inlet conduit 20 for conveying milk from an inner side (e.g., configured to face a nipple of breast 32) of nursing cup 10 to measurement unit 26. Outlet conduit 22 conveys milk from measurement unit 26 back to artificial nipple 12 of nursing cup 10. Artificial nipple 12 includes structure to enable the milk to flow into mouth 45 of a nursing child.

As shown, artificial nipple 12 is placed over the actual nipple of breast 32. However, an artificial nipple or other structure configured to deliver milk to mouth 45 may be situated elsewhere on nursing cup 10, or on a separate structure not necessarily configured for placement on breast 32.

Conduit system 34 may include a single enclosing tube, sheath, sleeve, or conduit for enclosing both inlet conduit 20 and outlet conduit 22, as shown in FIG. 1. Conduit system 34 may include inlet conduit 20 and outlet conduit 22 that are separated from one another, as shown in FIG. 2. Inlet conduit 20, outlet conduit 22, or both, may include one or more of a tube, pipe, channel, wick, or other structure suitable for conducting a flow of milk.

Measurement unit 26 may be configured to measure, or enable measurement of, a quantity or flow rate of milk flowing through conduit system 34, or a quality of the milk. Measurement unit 26 is configured to be located lateral to mouth 45 during nursing. Measurement unit 26 may be located lateral to nursing cup 10.

Nursing cup 10 may include an at least partially flexible material. The material may include tape, rubber, silicone, plastic, nylon, paper, polymer, isoprene, latex, or another suitable material or any combination of suitable materials. Nursing cup 10 may include a single layer of material or several layers. Nursing cup 10 may be disposable or may be sterilizable. Nursing cup 10 may be shaped to fit conveniently on breast 32 and into mouth 45.

Operation of nursing monitoring device 100 may be responsive to a pressure difference between mouth 45 and breast 32. Measurement unit 26 may be operable by the pressure difference (e.g., mechanical forces) or by another mechanical or electrical power source, such as a battery.

Nursing monitoring device 100 may include a processing unit 38. For example, measurement unit 26 may be configured to produce an electrical or electromagnetic signal indicative of a measured quantity. The signal may be conveyed to processing unit 38. For example, processing unit 38 may be configured to convert a signal that is received from measurement unit 26 to an interpreted result. Processing unit 38 may be configured to (e.g., may include a processor programmed to or circuitry designed to) process or analyze incoming data from measurement unit 26. Processing unit 38 may be configured to calibrate incoming data from measurement unit 26. Processing unit 38 may be configured to store data, or an interpretation of the data, e.g., on a local or remote data storage device.

A single processing unit 38 may be connectable to two or more measurement units 26. For example, each of the measurement units may measure milk flow from different breasts of a single nursing mother (e.g., when breastfeeding two children, such as twins, concurrently, or when alternating feeding between breasts), or from different nursing mothers (e.g., via a wireless connection in a comparative study). Processing unit 38 may be provided with a user operable control 53 (FIG. 5) that enables selection among various connected measurement units.

Figure 5:
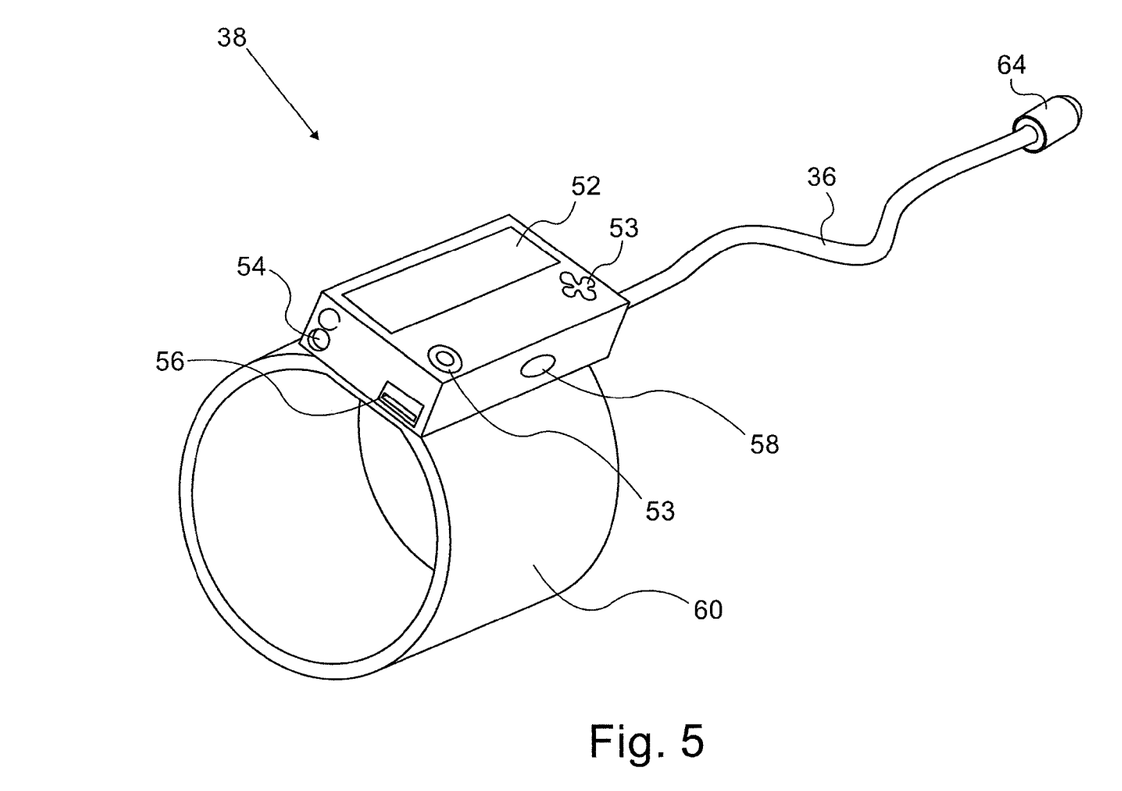
FIG. 5 is a schematic drawing of a processor unit of a nursing monitoring device, in accordance with an embodiment of the present invention.

An output based on the interpreted result may be displayed on display screen 52 of processing unit 38. For example, the displayed result may include a measured quantity, an interpretation of the measured quantity (e.g., "good," "poor," or other interpretation), a graphical display indicating a measured quantity or a change or trend of the measured quantity, or another displayable output based on the measured quantity or interpreted result. Output may be displayed or conveyed in another manner, visually (e.g., indicator lights, dial, or otherwise), audibly (e.g., tone or other audible signal), tactilely (e.g., vibrator, temperature change, or other tactile signal), or otherwise.

A connection between measurement unit 26 and processing unit 38 may be via a data cable 36 (e.g., electrical or optical), or may be wireless. Processing unit 38 may communicate with other computers, processors, or processing units. A single processing 38 unit may be connected to two or more measurement units 26.

Processing unit 38 may be mounted or placed in a location for convenient access by a user, such as a nursing mother, a consultant or advisor, a physician, nurse, or other healthcare provider, or another person. For example, processing unit 38 may be mounted on a wrist strap 60 to enable convenient access by a nursing mother. As another example, processing unit 38 may be suspended from a neck band, e.g., to enable concurrent connection to two measurement units 26 of two nursing monitoring devices 100, one on each breast. Processing unit 38 may be attachable (e.g., using a clip or pin) to an article of clothing (e.g., sleeve, strap, belt, lapel, pocket, or other part of an article of clothing) or to piece of furniture (e.g., to an arm of a chair), or may be otherwise mountable.

Measurement unit 26 may include, or enable access to (e.g., by a bypass tube or by directing a fraction of the flowing milk to an external collection tube or container) one or more measurement or other devices such as, for example, a gear pump or flowmeter, a membrane movement meter, an inflatable balloon meter, a piston meter, a nutating disk displacement meter, an oval gear meter, a helical gear meter, a positive displacement meter, a positive cavity meter, an interferometer, a spectrophotometer, an acoustic sensor, a timer, a thermometer, litmus paper, a bio-sensor, a sealed transparent window (e.g., enabling visual inspection of flowing milk), or other device. A sample of the milk may be cultured to enable detection of bacterial or fungal infection or other conditions. Measurement unit 26 may be configured to measure one or more quantities related to milk flow or quality. Such quantities may include, for example, feeding time, milk volume, flow velocity, milk viscosity, chemical gradients, fat content, temperature, pH level, optical reflection, optical absorption, sonic reflection, ultrasonic reflection, or another relevant quantity. Measurement unit 26 may enable a qualitative, relative, or subjective evaluation of the milk (e.g., via a window).

Figure 3:
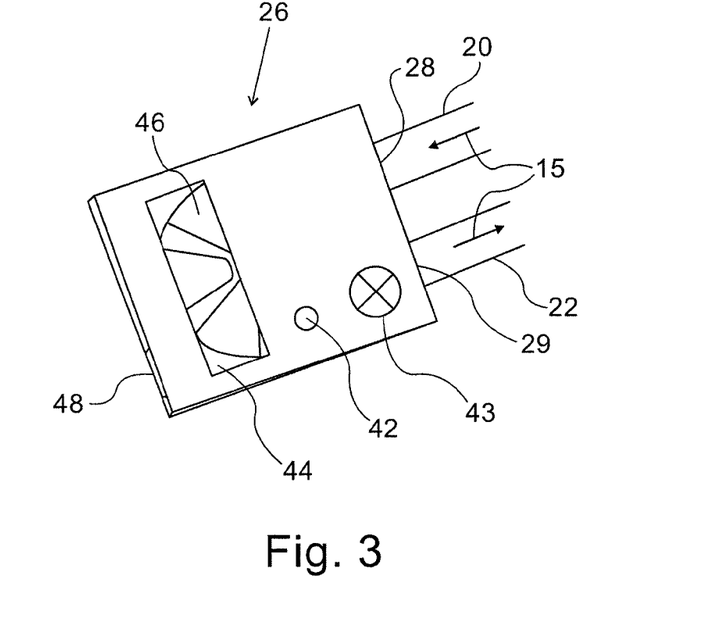
FIG. 3 is a schematic drawing of a measurement unit of a nursing monitoring device, in accordance with an embodiment of the present invention.

FIG. 3 is a schematic drawing of a measurement unit of a nursing monitoring device, in accordance with an embodiment of the present invention.

Measurement unit 26 may be sterilizable. Milk from inlet conduit 20 may flow into measurement unit 26 via inlet port 28. Milk may flow out of measurement unit 26 via outlet port 29 into outlet conduit 22.

Measurement unit 26 may include outlet valve 43 for extracting a specimen of the milk. For example, an extracted specimen may be introduced into a tube or connector for testing by an external testing or measurement device.

Measurement unit 26 may include a window 44. Window 44 may enable visual inspection of the milk or of milk flow 15.

Measurement unit 26 may include one or more mechanical flowmeter components 46. For example, mechanical flowmeter components 46 may include a rotor, as shown, or another mechanical flowmeter component. The rotor (or other component) may rotate (or be translated, or may expand, or otherwise move) at a speed or in another manner that is indicative of the flow rate. Rotation of the rotor may be visually viewed via window 44. Measurement unit 26 may include an electronic (e.g., optical, electromagnetic, or mechanical) sensor 42 (e.g., a rotation counter or other counter for counting passage of one or more distinguished regions of mechanical flowmeter component 46) that is configured to convert a sensed motion of mechanical flowmeter component 46 into an electronic signal. The electronic signal may be indicative of a flow rate or a volume (or mass) of milk flow 15.

For example, electronic sensor 42 may include one or more sensing units. A sensing unit may include a combination of a signal transmitting device and a signal receiving device. For example, a sensing unit may include a combination of sound transmitter (e.g., speaker) and a sound sensor (e.g., microphone), a radiation transmitter (e.g., a light emitting diode, e.g., in the infrared spectral range) and a light sensor (e.g., photodiode), or other combinations. The combination may be connected to a suitable potentiometer for conversion of a sensed count of rotations to an electronic signal. A combination of an optical transmitter and sensor may also be used to measure optical density or spectral transmission of the milk. The sensing unit may include a piezoelectric sensor, a reed sensor, an interferometer, an indicator tank (for visual examination), a strobe (e.g., to enable quantitative visual measurement), or another suitable component.

Measurement unit 26 may include data port 48. Data port 48 may enable transmission of the electronic signal to processing unit 38 (FIG. 1). Data port 48 may include a connector or socket for connecting to a data cable 36 (FIG. 1), or may include a suitable transmitter or transceiver for wireless communication with processing unit 38. In some cases, operation of measurement unit 26 may be controlled via a command that is received from another device (e.g., processing unit 38) via data port 48.

In some cases, mechanical flowmeter component 46, e.g., in the form of a rotor or other suitable device, may be operated as a pump or impeller to increase or decrease the flow rate of milk flow 15. For example, measurement unit 26 may include an electric motor that is operable in accordance with a command or signal that is received from an outside controller (e.g., incorporated into processing unit 38).

Since the measuring-device (26) need not fit between the breast and the mouth of the nursing child, dimensions of measurement unit 26 are not limited by such a constraint. Miniaturization of components of measurement unit 26 may not be required, thus enabling avoidance of the extra cost of manufacturing miniaturized components. A volume measurement scale of measurement unit 26 may be flexible. The scale may be as small as $10^{-6}$ liter, may be $10^{-5}$ liter, $10^{-4}$ liter, $10^{-3}$ liter, or another volume scale.

In accordance with an embodiment of the present invention, a nursing monitoring device may be provided with an artificial nipple to transfer milk from a breast to a mouth of a nursing child.

Figure 4:
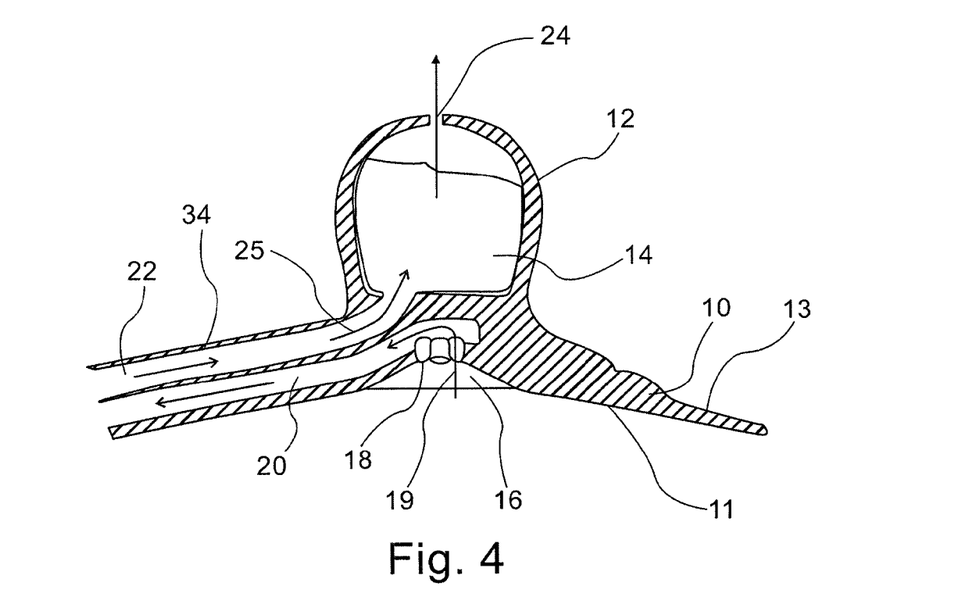
FIG. 4 is a schematic cross section of an artificial nipple of a nursing monitoring device, in accordance with an embodiment of the present invention.

FIG. 4 is a schematic cross section of an artificial nipple of a nursing monitoring device, in accordance with an embodiment of the present invention.

A portion of nursing cup 10 of a nursing monitoring device is formed into artificial nipple 12. Inner surface 11 of nursing cup 10 is configured to face inward, toward the surface of the breast. For example, a compartment or chamber in the form of inlet space 16 may be configured to be placed over a nipple of the breast. Outer surface 13 of nursing cup 10 is configured to face outward, e.g., toward a nursing child. Artificial nipple 12 on outer surface 13 is configured to fit into the mouth of a nursing child.

Milk inflow 19 represents a flow of milk from the nipple, via inlet space 16 and inlet opening 18 into inlet conduit 20. The milk in inlet conduit 20 may flow into a measurement unit of the nursing monitoring device. Milk outflow 25 represents a flow of milk back from the measurement unit via outlet conduit 22 and into a compartment or chamber in the form of outlet space 14. Milk in outlet space 14 may flow outward through outlet opening 24, e.g., into the mouth of a nursing child.

FIG. 5 is a schematic drawing of a processor unit of a nursing monitoring device, in accordance with an embodiment of the present invention.

Processing unit 38 includes a data cable 36 whose distal end terminates in plug 64. Plug 64 may be plugged into an appropriate socket or connector (e.g., data port 48, FIG. 3) of a measurement unit of the nursing monitoring device. Alternatively or in addition, processing unit 38 may be connected wirelessly to the measurement unit. Processing unit 38 is mounted on wrist strap 60. Alternatively or in addition, processing unit 38 may be otherwise clipped on or worn.

Processing unit 38 may include a display screen 52. Display screen 52 may be operated to display one or more results of a measurement of the flowing milk. Such results may include a quantity, a quality, a temperature, total nursing time, nursing statistics, calories, or another result related to the milk. Other information that may be displayed is an amount of supplementary food provided to the child, which breast was used or separate results relating to each breast, or other information.

Processing unit 38 may be configured to provide a real-time alert, alarm or indication of a situation requiring attention. For example, such a situation may include underfeeding, contaminated milk, low value milk, and end of feeding. Processing unit 38 may include an audible output device 58 (e.g., beeper, buzzer, speaker, bell, or other device) or a vibrator or similar element, to provide an audible or tactile alert.

Processing unit 38 may include a Universal Serial Bus (USB) plug 56, earphone jack 54, and user operable controls 53 (e.g., buttons or other controls).

In some cases, processing unit 38 and a measurement unit may be incorporated into a single device or into a single housing.

A method for monitoring breastfeeding may be implemented, in accordance with an embodiment of the present invention. Reference is made to FIGS. 1-5.

Inlet opening 18 is placed over a nipple of breast 32. For example, nursing cup 10 may be placed on breast 32. Placement of inlet opening 18 enables milk flow 15 to flow from the nipple via inlet conduit 20 through measurement unit 26 and into outlet conduit 22. Outlet opening 24 of outlet conduit 22 is placed at a position that is accessible to mouth 45 of a nursing child, such that measurement unit 26 is located laterally to mouth 45.

Measurement unit 26 may be operated to measure a property of milk flow 15. For example, operation of measurement unit 26 may include observing the milk flow 15 via window 44, extracting a sample of milk flow 15 via outlet valve 43, or operating a measurement device. A measurement device may include a flowmeter, an interferometer, a spectrophotometer, an acoustic sensor, a timer, and a thermometer. Electronic output from a measurement device may be transmitted via data cable 36 to a processing unit 38.

A nursing monitoring device, in accordance with embodiments of the present invention, may be utilized, for example, in determining factors that influence feeding decisions, breastfeeding and/or bottle initiation rates, as well as breastfeeding duration. For example, measurements of breast feeding may be correlated with other factors (e.g., demographics, prenatal and postnatal care, sources of breastfeeding information, timing of decision, preference, duration of breastfeeding, or another factor) to determine factors that influence decisions regarding breastfeeding.

A nursing monitoring device, in accordance with embodiments of the present invention, may be utilized in answering questions of concern to nursing mothers. Such questions may include how much does the baby eat, and has the baby eaten enough? A nursing monitoring device, in accordance with embodiments of the present invention, may provide an accurate measurement while not interfering (non-obtrusive, noninvasive, and comfortable) with the nursing mother and child.

A nursing monitoring device, in accordance with embodiments of the present invention, may provide an exact quantity (volume) of the intake breast milk as a function of time and the side of the breast. Providing accurate information with regard to the quantity and quality of the breastfed milk may provide reassurance to the mother and others to help overcome an insecurity or doubt that could interfere with breastfeeding.

A nursing monitoring device, in accordance with embodiments of the present invention, may be used to correlate feeding statistics with a count of wet diapers or with weight gain (after feeding relative to before feeding). This may determine the predictive value of diaper or weight measurements with respect to the effectiveness of breastfeeding.

The device may be utilized to assist in monitoring feeding from different breasts, e.g., in a case of breastfed twins or other multiple births. Milk production is known to vary as a function of the frequency of breastfeeding and the quantity of milk in the breast bulk. The frequency of removing the milk from the breast influences the total quantity of milk which is produced every day. The device may be utilized to monitor quality and composition of the milk. It is known that the milk composition during the morning hours is different from that of the evening hours. For example, the percentage of fat is lower during the morning hours than that of the evening hours. This difference in composition causes difference in quantity of milk release. Mothers might stop breastfeeding if they wrongly assume that they do not produce enough milk during the evening hours, which may be prevented by monitoring milk content.

A nursing monitoring device, in accordance with embodiments of the present invention, e.g., that is provided with pumping capability, may be utilized to assist when breastfeeding is difficult. For example, premature babies and weak babies may find breastfeeding difficult and may tend to prefer bottles. Other babies that have experienced bottles may find it difficult to restart breastfeeding. Such a pumping capability may assist in continuing breastfeeding under such circumstances.

A nursing monitoring device, in accordance with embodiments of the present invention, may be utilized to assist in optimizing a feeding schedule, including alternation between breasts. Sometimes, it is important to control the quantity of milk production. Milk production is influenced by a biofeedback mechanism. When the breast is full of milk, milk production is minimal, and when the milk is frequently removed; the milk production is increased. Controlling this mechanism allows to optimize the quantity of milk for a particular nursing mother.

A nursing monitoring device, in accordance with embodiments of the present invention, may enable measurement or testing of milk quality. For example, contaminated milk, or milk otherwise of poor quality, that could pose a health hazard to the nursing child may be detected. Milk may be contaminated due to a disease or to tainted food that was consumed by the nursing mother. Samples of the milk may be collected from the milk flow, e.g., via a valve. The sampled milk may be tested, e.g., using an indicator such as bio-sense paper, inflammation-test paper, or another indicator. In response to detection of contaminated milk, supplements or medication may be recommended in a timely manner.

A nursing monitoring device, in accordance with embodiments of the present invention, may be designed in so as to function in an effective or optimal manner. Design considerations include, for example, materials, dimensions, curvatures, positioning relative to the nipple height, ratio between inlet and outlet diameters, types of flowmeter, operation for various fluids, or other considerations. Since an analytical or numerical evaluation of a design may be cumbersome, complicated, or inaccurate, an analog simulator (e.g., with mechanical components substituted for the nursing mother and child) may be utilized to empirically evaluate a design.

Figure 6:
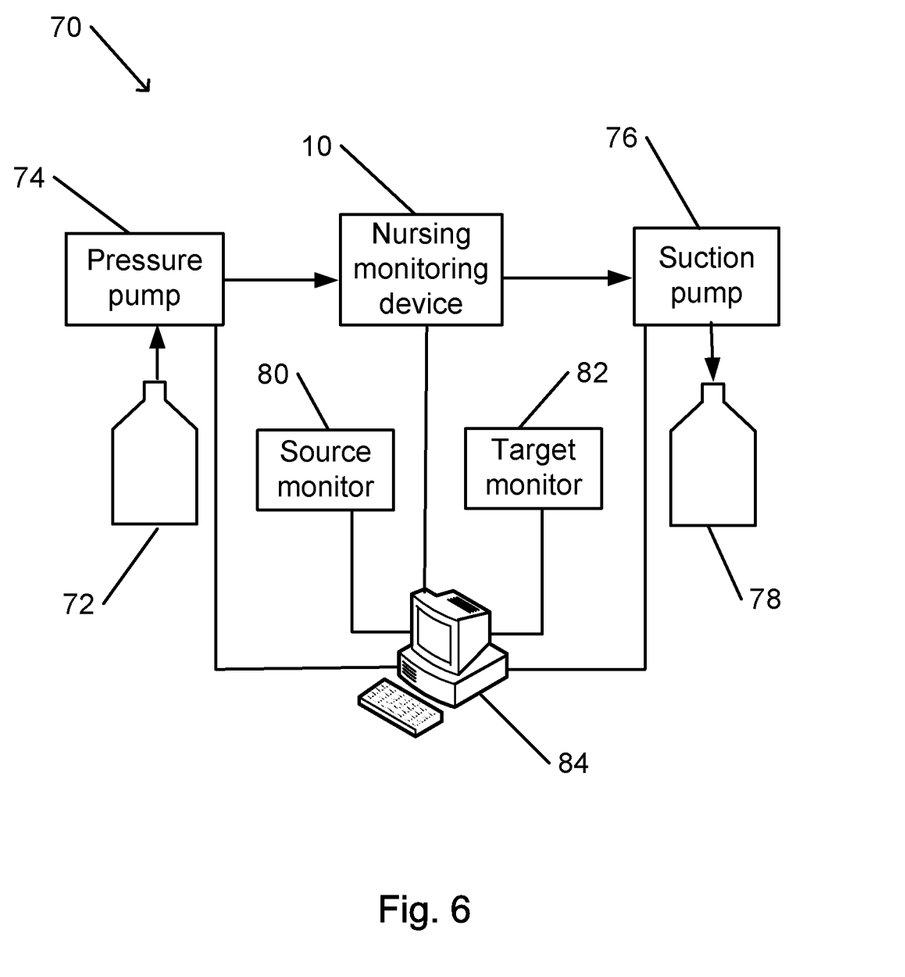
FIG. 6 is a schematic diagram of a system for evaluation of operation of a nursing monitoring device, in accordance with an embodiment of the present invention.

FIG. 6 is a schematic diagram of a system for evaluation of operation of a nursing monitoring device, in accordance with an embodiment of the present invention.

Evaluation system 70 is configured to empirically evaluate operation and performance of nursing monitoring device 10.

Operation of a nursing breast may be simulated by source container 72 and pressure pump 74. For example, pressure pump 74 may include a peristaltic pump or another type of positive displacement or other pump. The combination of source container 72 and pressure pump 74 may simulate the positive pressure of milk that is released by a nipple Contents of source container 72 may be monitored by source monitor 80. For example, source monitor 80 may include a scale or volume sensor for determining a mass, weight, or volume of the liquid that remains in source container 72.

Nursing monitoring device 10 in evaluation system 70 may include a complete nursing monitoring device, or an arrangement of components that simulates operation of a nursing monitoring device.

Operation of a mouth of a nursing child may be simulated by suction pump 76 and target container 78. The combination of target container 78 and suction pump 76 may simulate the negative pressure of sucking by the child's mouth Contents of target container 78 may be monitored by target monitor 82. For example, target monitor 82 may include a scale or volume sensor for determining a mass, weight, or volume of the liquid that is transferred to target container 78 via nursing monitoring device 10.

Computer 84 may be configured to receive data from source monitor 80, target monitor 78, nursing monitoring device 10, pressure pump 74, suction pump 76, or any combination of the above. Computer 84 may be configured to receive data from other sensors or devices (e.g., thermometer, flowmeter, pressure meter, or other device). In addition, computer 84 may be configured to control operation of one or more of source monitor 80, target monitor 78, nursing monitoring device 10, pressure pump 74, and suction pump 76. Computer 84 may be configured to control operation of one or more valves or other components of evaluation system 70.

Computer 84 may be configured to analyze or evaluate the received data so as to evaluate operation of a particular design or configuration of nursing monitoring device 10. For example, computer 84 may evaluate an accuracy of measurement by nursing monitoring device 10, a degree to which nursing monitoring device 10 interferes with flow of milk from supply container 72 to target container 78.

For example, a typical operation of evaluation system 70 may evaluate a fluid in the form of milk. Milk may be characterized by a density of 9.3 g/ml$^3$, a fat content of 20%, viscosity of 8 cP, and a lactose concentration of 2%. Pressure pump 74 may be a peristaltic pump with a pressure amplitude of 0.03 atmosphere with a pressure function of 0.15 ml bursts at 2 Hz. The conduit structure of nursing monitoring device 10 may be cylindrical with one 180° turn, a length of 50 mm, diameter of 3 mm, and made of nylon. The flowmeter of nursing monitoring device 10 may be a positive displacement flowmeter. Suction pump 76 may be a rotor pump with a pressure amplitude −0.2 atmosphere and a constant pressure function. These parameters may be kept constant throughout a session of measurements. Assuming Poiseuille's law (a coarse guess), the resistivity of the milk flow is inversely proportional to the conduit radius to the fourth power. Thus, the diameter of the conduit may be the factor with the most influence on the flow resistivity.

Quantities measured with evaluation system 70 may include, for example, time for milk to enter the conduit (e.g., from source container 72), time to enter the mouth (e.g., to target container 78), weight or volume of transferred milk, pressure at pressure pump 74 or at suction pump 76, fluid temperature, ambient temperature, or other quantities. Measured quantities may be compared with design criteria. For example, in some cases, design criteria may include a maximum transfer time from source container 72 to target container 78 (e.g., 5 seconds, or another value), flowmeter error (e.g., no more than 0.97%, or another value), flow resistance (e.g., no more than 5 atmospheres per milliliter in a single suck, or another value), minimum transfer pressure (e.g., no more than 0.02 atmosphere, or another value), or additional or other criteria.

The invention claimed is:

1. A nursing monitoring device comprising:
    a nursing cup configured to be placed over a nipple of the breast and comprising inner and outer surfaces that face away from each other, the nursing cup further comprising an artificial nipple positioned on the outer surface of the nursing cup and configured to fit into a mouth of a nursing child;
    a single inlet conduit with an inlet opening, wherein the inlet opening is located on the inner surface of the nursing cup, and wherein the inlet opening is configured to enable milk that is released from the nipple of said breast to enter into the single inlet conduit; and
    a single outlet conduit with a single outlet opening in fluid association with the artificial nipple, the single outlet opening configured to enable the released breast milk to flow from the single outlet conduit into and through the artificial nipple to enter the mouth of the nursing child; and
    a measurement unit positioned away from the artificial nipple, fluidly connected to the single inlet conduit and to the single outlet conduit, and configured to enable measurement of a property of said milk that (a) is released from the nipple, (b) enters into the single inlet conduit through the inlet opening, and (c) flows from said single inlet conduit through the measurement unit and then through the single outlet conduit and outlet opening into and through the artificial nipple and into the mouth of the nursing child in a single flowpath, the single outlet conduit being sufficiently long for placement of the measurement unit laterally to the artificial nipple and said child's mouth.

2. The device of claim 1, wherein the measurement unit comprises a flowmeter.

3. The device of claim 2, wherein the flowmeter comprises a positive displacement flowmeter.

4. The device of claim 3, wherein the positive displacement flowmeter comprises a gear.

5. The device of claim 2, wherein the flowmeter is selected from a group of flowmeter types consisting of a membrane movement meter, an inflatable balloon meter, a piston meter, a nutating disk displacement meter, an oval gear meter, and a helical gear meter.

6. The device of claim 2, wherein the flowmeter is configured to produce an electronic signal that is indicative of a volume or of flow rate of the milk that flows through the flowmeter.

7. The device of claim 6, wherein the flowmeter comprises a rotation counter.

8. The device of claim 1, wherein the measurement unit comprises a window to enable visual examination of the milk.

9. The device of claim 1, wherein the measurement unit comprises a valve to enable extraction of a sample of the milk.

10. The device of claim 1, comprising a processing unit for processing data that is measured by the measurement unit, the processing unit being connectible via a data cable or via a wireless connection to the measurement unit.

11. The device of claim 10, wherein the processing unit comprises a display screen or an audible output device.

12. The device of claim 1, wherein the artificial nipple is attached to the nursing cup and the single outlet opening is located on an outer side of the nursing cup forming an opening into the artificial nipple.

13. The device of claim 12, wherein the single outlet opening is located opposite the inlet opening.

14. The device of claim 1, wherein the single inlet conduit and the single outlet conduit are enclosed in a single tube.

15. The device of claim 1, wherein the measurement unit comprises an interferometer, a spectrophotometer, an acoustic sensor, a timer, or a thermometer.

16. A method for monitoring breastfeeding, the method comprising:
   providing a nursing cup which comprises inner and outer surfaces that face away from each other, and an artificial nipple positioned on the outer surface of the nursing cup and configured to fit into a mouth of a nursing child;
   providing (a) a single inlet conduit that includes a single inlet opening located on the inner surface of the nursing cup, (b) a single outlet conduit that includes a single outlet opening in fluid association with the artificial nipple, and (c) a measurement unit fluidly associated with the inlet and outlet conduits;
   placing the nursing cup over a nipple of a breast to enable milk that is released from said nipple to enter the single inlet conduit via the inlet opening and to flow via the single inlet conduit the measurement unit and then to the single outlet conduit;
   placing the artificial nipple at a position that is accessible to the mouth of the nursing child, wherein the measurement unit is positioned away from the nursing cup, and the single outlet conduit is sufficiently long for placement of the measurement unit laterally to the artificial nipple and said child's mouth; and
   operating the measurement unit to measure a property of the milk that (a) is released from the nipple, (b) enters into the single inlet conduit through the single inlet opening, and (c) flows from said single inlet conduit through the measurement unit and then through the single outlet conduit and single outlet opening into and through the artificial nipple and into the mouth of the nursing child in a single flowpath.

17. The method of claim 16, wherein operating the measurement unit comprises observing the milk via a window, extracting a sample of the milk, or operating a measurement device selected from a group of measurement devices consisting of a flowmeter, an interferometer, a spectrophotometer, an acoustic sensor, a timer, and a thermometer.

18. The method of claim 16, wherein the single outlet opening is located on an outer side of the nursing cup, and wherein said nursing cup is placed on the nipple in order to place the inlet opening on the nipple.

19. A nursing monitoring device comprising:
   a nursing cup comprising inner and outer surfaces that face away from each other, with the nursing cup being configured to be placed over a nipple of the breast;
   an artificial nipple positioned on and attached to the outer surface of the nursing cup and configured to fit into a mouth of a nursing child;
   a milk conduit comprising:
      a first conduit portion having an inlet opening located on the inner surface of the nursing cup, wherein the inlet opening is configured to enable milk that is released from the nipple of said breast to enter into the first conduit portion; and
      a second conduit portion having an outlet opening in fluid association with the artificial nipple, wherein the outlet opening is configured to enable the released breast milk to flow from the second conduit portion into and through the artificial nipple to enter the mouth of the nursing child; and
   a measurement unit in fluid association with the first and second conduit portions and positioned away from the artificial nipple, wherein the measurement unit is configured to enable measurement of a property of the milk that (a) is released from the nipple, (b) enters into the first conduit portion from said single inlet opening; and (c) flows through the first conduit portion to the measurement unit and then through the second conduit portion and single outlet opening into and through the artificial nipple and into the mouth of the nursing child in a single flowpath, wherein the second conduit portion is sufficiently long for placement of the measurement unit laterally to the artificial nipple and the child's mouth.

* * * * *